United States Patent
Ohta et al.

(10) Patent No.: US 7,918,603 B2
(45) Date of Patent: Apr. 5, 2011

(54) RADIOGRAPHIC IMAGING TABLE

(75) Inventors: Yasunori Ohta, Kanagawa (JP); Keiji Tsubota, Kanagawa (JP); Yutaka Yoshida, Kanagawa (JP); Naoyuki Nishino, Kanagawa (JP); Kazuyuki Hasegawa, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/561,281

(22) Filed: Sep. 17, 2009

(65) Prior Publication Data
US 2010/0080360 A1 Apr. 1, 2010

(30) Foreign Application Priority Data
Sep. 26, 2008 (JP) ................. 2008-247315

(51) Int. Cl.
*A61B 6/00* (2006.01)
(52) U.S. Cl. ...................................... 378/189
(58) Field of Classification Search .............. 378/189, 378/98.8
See application file for complete search history.

(56) References Cited

U.S. PATENT DOCUMENTS
2003/0021384 A1 * 1/2003 Ohkoda ................ 378/177
2006/0285643 A1 * 12/2006 Molz et al. ............ 378/101

FOREIGN PATENT DOCUMENTS
| JP | 2000-206636 A | | 7/2000 |
| JP | 2003010175 A | * | 1/2003 |
| JP | 2004-160263 A | | 6/2004 |
| JP | 2004-173907 A | | 6/2004 |

* cited by examiner

Primary Examiner — Chih-Cheng G Kao
(74) Attorney, Agent, or Firm — Solaris Intellectual Property Group, PLLC (57) ABSTRACT

There is provided a radiographic imaging table including: a test object mounting plate capable of allowing radiation to penetrate therethrough, on which a test object is mounted; a detector mounting plate which is disposed under the test object mounting plate to movably mount a radiographic image detector which detects radiation penetrating the test object and the test object mounting plate, and which generates an image according to the detected radiation; and a connection device which is disposed on the detector mounting plate such that it is connectable to the radiographic image detector in order to perform at least one of charging the radiographic image detector mounted on the detector mounting plate or facilitating communication between the radiographic image detector and an external device.

14 Claims, 7 Drawing Sheets

RADIOGRAPHIC IMAGING TABLE

CROSS-REFERENCE TO RELATED APPLICATION

This application is based on and claims priority under 35 USC 119 from Japanese Patent Application No. 2008-247315 filed on Sep. 26, 2008, the disclosure of which is incorporated by reference herein.

BACKGROUND

1. Field of the Invention

The invention relates to a radiographic imaging table and, more particularly, to a radiographic imaging table used for imaging using a portable radiographic image detector.

2. Description of the Related Art

Recently, a flat panel detector (FPD) that is constructed by disposing a radiation sensitive layer on a thin film transistor (TFT) active matrix substrate has been put to practical applications. The FPD can directly convert an X-ray into digital data. A portable radiographic image detecting device (hereinafter, referred to as an " electronic cassette") for generating image data indicating a radiographic image represented by a radiation penetrating a test object and being irradiated by using the FPD and storing the generated image data has been put to practical applications.

Since the electronic cassette has good portability, a test object loaded on a stretcher or a bed can be imaged. In addition, since an imaged portion can be adjusted by changing a position of the electronic cassette, even an immobile patient as an example of the test object can be adaptively imaged.

Such a portable electronic cassette is embedded with a memory for storing the image data of the captured images and a battery. The electronic cassette is inserted into a dedicated cassette stand so as to transmit the image data to an external device, that is, a console or to charge the embedded battery (for example, refer to Japanese Patent Application Laid-Open (JP-A) No. 2000-206636). However, every time the electronic cassette used with a bed is to be charged or the image data is to be transmitted, the electronic cassette needs to be moved to the cassette stand. Particularly, there is great inconvenience in a case where the bed and the cassette stand are separated from each other over a long distance.

Therefore, disclosed is an electronic cassette provided with a cable which has a connector at an end thereof so as to be connected to an external device. Even in a case where the electronic cassette is inserted between a bed and a human body, the connector is designed to protrude from the human body, so that the electronic cassette during use on the bed can be easily connected to the external device (for example, refer to Japanese Patent Application Laid-Open (JP-A) No. 2004-173907)

In addition, disclosed is an X-ray imaging apparatus in which a cassette inserting position is provided under a top board of a bed (for example, refer to Japanese Patent Application Laid-Open (JP-A) No. 2004-160263).

However, in the electronic cassette disclosed in JP-A No. 2004-173907, since the electronic cassette is inserted between the bed and the to-be-tested person, the person may feel unpleasant. In addition, since the cable or the connector exists on the bed, there is a problem in that the cable or the connector may interfere with the loading of the to-be-test person on the bed or the handling of the electronic cassette by an operator. In addition, there is a problem in that the photographable portion may be limited depending on a length of the cable.

In addition, in the X-ray imaging apparatus disclosed in JP-A No. 2004-160263, there is a problem in that the cassette inserting position is fixed and the photographable portion is limited.

SUMMARY

An object of the invention is to provide a radiographic imaging table in which a cable or a connector cannot interfere with imaging and an imaged portion is also not limited even in a case where charging or data-transmitting of a radiographic image detector in the imaging table is performed.

In order to achieve the above object, a first aspect of present invention provides a radiographic imaging table including:

a test object mounting plate capable of allowing radiation to penetrate therethrough, on which a test object is mounted;

a detector mounting plate which is disposed under the test object mounting plate to movably mount a radiographic image detector which detects radiation penetrating the test object and the test object mounting plate, and which generates an image according to the detected radiation; and a connection device which is disposed on the detector mounting plate such that it is connectable to the radiographic image detector in order to perform at least one of charging the radiographic image detector mounted on the detector mounting plate or facilitating communication between the radiographic image detector and an external device.

In this manner, the charging of the radiographic image detector and the communication between the radiographic image detector and the external device can be performed in the state that the radiographic image detector remains on the radiographic imaging table. Since the connection device needed for the charging and the communication is provided to the detector mounting plate, the cable or the connector does not protrude on the test object mounting plate or from the side surface of the radiographic imaging table, and the cable or the connector cannot interfere with the imaging. In addition, the radiographic image detector can move on the substantially entire surface of the detector mounting plate to the position of the test object on the test object mounting plate, and the imaged portion is not limited. Moreover, since there is no need for inserting the radiographic image detector between the test object mounting plate and the test object, there is no load to the test object.

In addition, the radiographic imaging table according to the invention may be constructed to include a tray on which the radiographic image detector movably mounted on the detector mounting plate is mounted.

In addition, a tray connection member for connecting the radiographic image detector with the connection device may be provided to the tray. Accordingly, the connection device can be connected to the radiographic image detector in the state that the radiographic image detector remains mounted on the tray.

In addition, the tray may be movably provided in one of long-side and short-side directions of the detector mounting plate along a pair of second tracks which are movably provided along a pair of first tracks which are provided along the other of the long-side and short-side directions of the detector mounting plate, and the tracks may be constructed with rails or grooves. Accordingly, the movement of the radiographic image detector mounted on the tray can be more easily performed.

In addition, the first and second tracks may be constructed with rails made of a conductive member, and the charging of the radiographic image detector or the communication between the radiographic image detector and an external device may be performed through the first and second tracks. Accordingly, the charging or communication of the radiographic image detector mounted on the tray can be performed without movement of the tray to the position of the connection device disposed in a predetermined position, so that convenience can be improved.

In addition, a second aspect of the present invention provides a radiographic imaging table including:

a test object mounting plate capable of allowing radiation to penetrate therethrough, on which a test object is mounted;

a detector mounting plate which is disposed under the test object mounting plate to movably mount a radiographic image detector which detects radiation penetrating the test object and the test object mounting plate, and which generates an image according to the detected radiation; and a pair of first rails in one of a length or width direction of the detector mounting plate, a pair of second rails movably provided along the pair of first rails, and a tray provided so as to be capable of moving along the pair of second rails in the other of the length or width direction of the detector mounting plate, wherein the first and second rails comprise a conductive member, and charging of the radiographic image detector or communication between the radiographic image detector and an external device is performed through the first and second rails.

In addition, a radiation absorbing member may be disposed on a surface of the tray. Accordingly, there is no need for providing a radiation absorbing member to the radiographic image detector. The radiographic image detector can thus be constructed with a light weight.

In addition, a power supply unit may be disposed to an inner portion of the detector mounting plate or under the detector mounting plate to supply power, in a non-contact manner, to a power receiving member provided to the radiographic image detector through electromagnetic induction so as to receive a power for charging an embedded battery. Accordingly, at the time of charging, there is no need for connecting the electronic cassette to the connection device, so that convenience can be improved.

In addition, a third aspect of the present invention provides a radiographic imaging table including:

a test object mounting plate capable of allowing radiation to penetrate therethrough, on which a test object is mounted;

a detector mounting plate which is disposed under the test object mounting plate to movably mount a radiographic image detector which detects radiation penetrating the test object and the test object mounting plate, and which generates an image according to the detected radiation; and a power supply unit which is disposed at an inner portion of the detector mounting plate or under the detector mounting plate, to supply power in a non-contact manner to a power receiving member provided to the radiographic image detector through electromagnetic induction so that the power receiving member receives a power for charging an internal battery.

In addition, a radiation absorbing member may be disposed on a surface of the detector mounting plate. In a construction where the tray is not provided, by disposing the radiation absorbing member on a surface of the detector mounting plate, the radiographic image detector can be constructed with a light weight, similarly to the case where the radiation absorbing member is provided to the tray.

As described above, according to the radiographic imaging table of the invention, even in a case where charging or data-transmitting of a radiographic image detector in the imaging table is performed, there is an advantage in that a cable or a connector cannot interfere with imaging and an imaged portion is also not limited.

BRIEF DESCRIPTION OF THE DRAWINGS

Exemplary embodiments of the present invention will be described in detail based on the following figures, wherein.

DETAILED DESCRIPTION

Hereinafter, exemplary embodiments of the invention will be described in detail with reference to the accompanying drawings.

Figure 1:
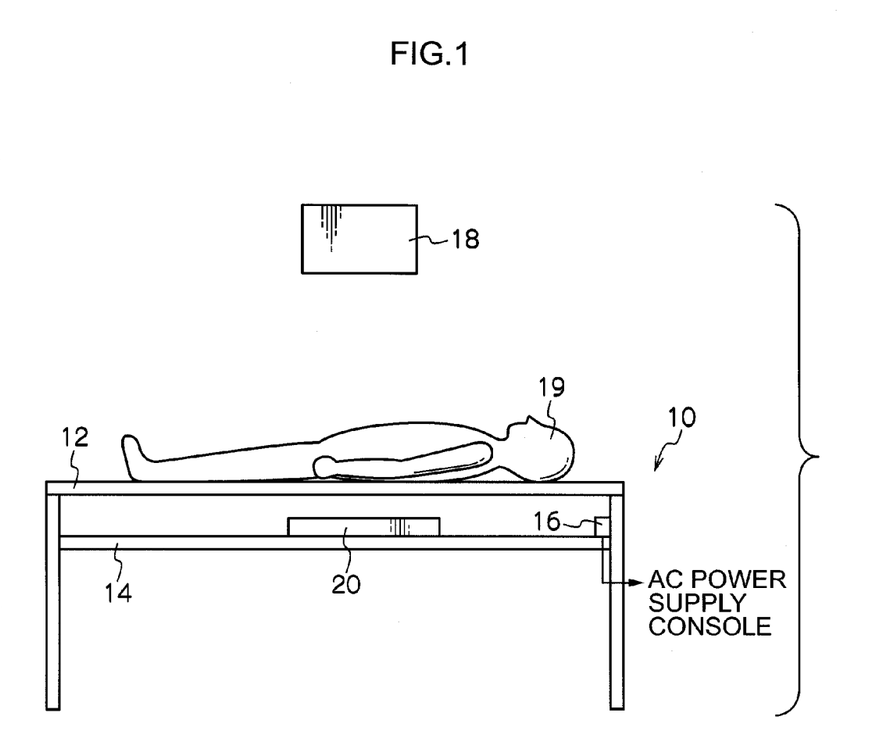
FIG. 1 is a schematic side view illustrating a radiographic imaging table according to a first exemplary embodiment.

As shown in FIG. 1, in a radiographic imaging table 10 according to a first exemplary embodiment, at the time of radiographic imaging, a test object 19 is loaded on a top board 12 described later. When radiographic imaging is commanded, a radiation generating unit 18 which generates a radiation such as an X-ray emits the radiation with a radiation amount according to predetermined imaging conditions. The radiation emitted from the radiation generating unit 18 penetrates the test object 19 positioned at an imaging position. The radiation containing image information penetrates the top board 12 to be irradiated on a portable radiographic image detecting device (hereinafter, referred to as an "electronic cassette") 20 mounted on a cassette mounting plate 14 described later. Accordingly, in the electronic cassette 20, the radiographic image is detected.

As the electronic cassette 20, a direct-conversion electronic cassette in which the radiation is directly converted to charges by using a radiation-charge conversion material such as amorphous selenium and an indirect-conversion electronic cassette in which the radiation is indirectly converted to charges by performing a radiation-photon conversion by using a fluorescent material such as gadolinium oxysulfide (GOS) or cesium iodide (CsI) and performing a photon-charge conversion by using a photoelectric conversion device such as a photodiode may be used.

The radiographic imaging table 10 includes the top board 12 capable of penetrating the radiation, on which the test object 19 is loaded, the cassette mounting plate 14 which is disposed under the top board 12 to mount the electronic cassette 20 thereon, and a connector 16 which is disposed on the cassette mounting plate 14, so that connection for charging of the electronic cassette 20 and transmitting of data can be provided. The top board 12 and the cassette mounting plate 14 have substantially the same shape. The radiographic imaging table 10 has a two-layer structure in which the cassette mounting plate 14 serves as the bottom layer and the top board 12 as the top layer.

The top board 12 is made of a material capable of penetrating a radiation and having a strength so that the test object 19 can be loaded. As the top board 12, for example, an acryl board, a carbon board, wood, or a combination thereof can be used.

In the cassette mounting plate 14, substantially the entire surface thereof is used for a region on which the electronic cassette 20 can be mounted, and the electronic cassette 20 can be disposed at a position corresponding to the position of the test object 19 loaded on the top board 12. In addition, a lead plate as a radiation absorbing member may be disposed on a surface of the cassette mounting plate 14, so that a back scattered radiation in the electronic cassette 20 can be absorbed. In this manner, since the lead plate is disposed on the surface of the cassette mounting plate 14, a lead plate provided to the electronic cassette 20 can be omitted. Therefore, the electronic cassette 20 can be constructed with a light weight.

Preferably, a gap between the top board 12 and the cassette mounting plate 14 is as short as possible. As the gap between the top board 12 and the cassette mounting plate 14 is increased, the distance between the test object 19 and the electronic cassette 20 is also increased, and thus, magnification imaging may be unintentionally performed. In terms of the handling of the electronic cassette 20, there is a need for providing a suitable empty gap. In case of outputting or displaying a captured image, image processing for obtaining an equally-magnified image by taking a reciprocal number of a magnification ratio corresponding to the gap between the top board 12 and the cassette mounting plate 14 may be performed.

Figure 2:
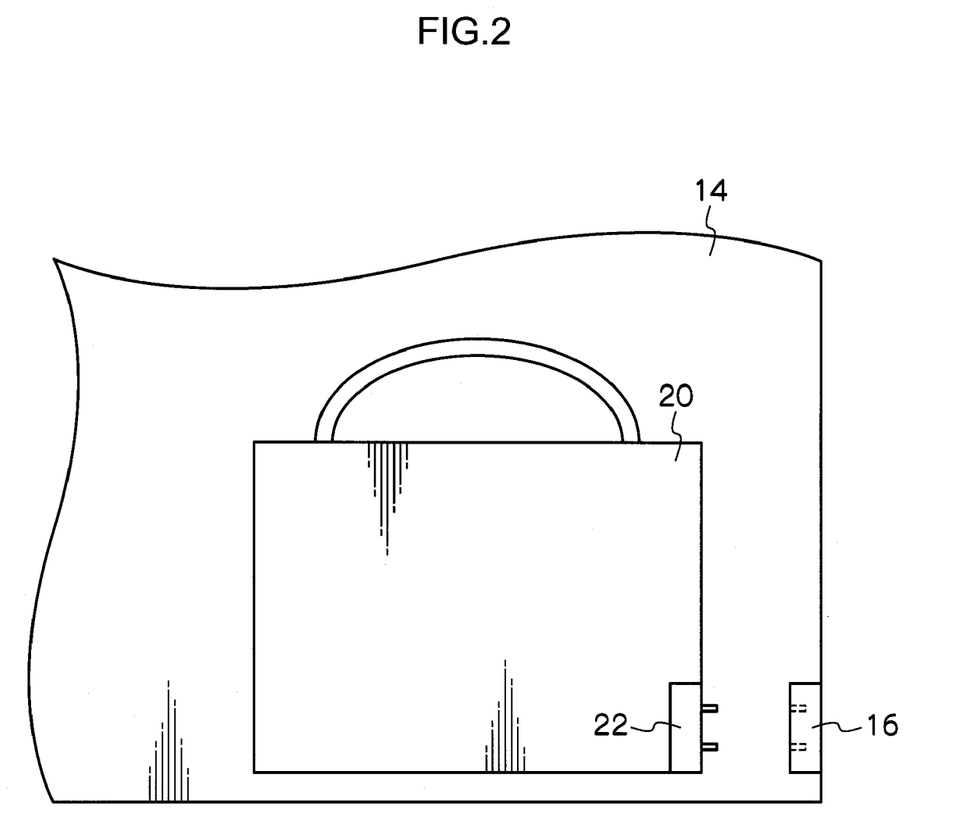
FIG. 2 is a schematic view illustrating a connector of the radiographic imaging table according to the first exemplary embodiment.

As shown in FIG. 2, the connector 16 is disposed at a portion (for example, a corner) of the cassette mounting plate 14. The connector 16 is connected through a cable to an AC power supply and an external device, that is, a console so as to be connected to a cassette connection member 22 provided to the electronic cassette 20. Accordingly, the electronic cassette 20 can be connected to the AC power supply and the console.

Next, operations of the radiographic imaging table 10 according to the first exemplary embodiment will be described.

At the time of imaging, the test object 19 is loaded on the top board 12. An operator mounts the electronic cassette 20 on the cassette mounting plate 14. While checking the loaded position of the test object 19 on the top board 12, the operator moves the electronic cassette 20 to a corresponding position on the cassette mounting plate 14. Alternatively, before the test object 19 is loaded on the top board 12, the electronic cassette 20 may be mounted on the cassette mounting plate 14 in advance.

When the imaging is ended, the operator moves the electronic cassette 20 on the cassette mounting plate 14 to the position where the connector 16 is disposed, so that the cassette connection member 22 is connected to the connector 16. Since the connector 16 is connected through a cable to the AC power supply, power is supplied from the AC power supply, so that the battery embedded in the electronic cassette 20 is charged with power as much as consumed power. In addition, since the connector 16 is connected through a cable to the console, in response to an operator's command of transmitting image data, the image data stored in a memory provided in the electronic cassette 20 is transmitted to the console.

In addition, the console is connected to a radiology information system (RIS, not shown) which collectively manages radiographic image information or others handled in the department of radiology of a hospital. The RIS is connected to a hospital information system (HIS, not shown) which collectively manages medical information of a hospital. Therefore, in the console, since power that is to be consumed by the electronic cassette 20 in the next imaging can be requested, the charging with the power corresponding to the to-be-consumed power can be controlled.

When the charging of the battery or the transmitting of data is ended, the cassette connection member 22 is disconnected from the connector 16. The electronic cassette 20 remains mounted on the cassette mounting plate 14 for the next imaging.

In the radiographic imaging table according to the first exemplary embodiment, since the connector for the charging or the transmitting of data is disposed to the cassette mounting plate disposed under the top board, the cable or the connector cannot interfere with the loading or unloading of the test object, that is, a patient or the operator's handling of the electronic cassette in comparison with a case where the cable or the connector is disposed on the top board or to a side portion of the bed. In addition, since the electronic cassette can be mounted on any position of the cassette mounting plate, the imaged portion is not limited and there is no pulling of the cable. In addition, since the inserting of the electronic cassette between the top board and the test object is unnecessary, the load to the test object can be lowered.

Next, a radiographic imaging table according to a second exemplary embodiment will be described. The same elements as those of the radiographic imaging table 10 according to the first exemplary embodiment are denoted by the same reference numerals, and the description thereof is omitted.

Figure 3A:
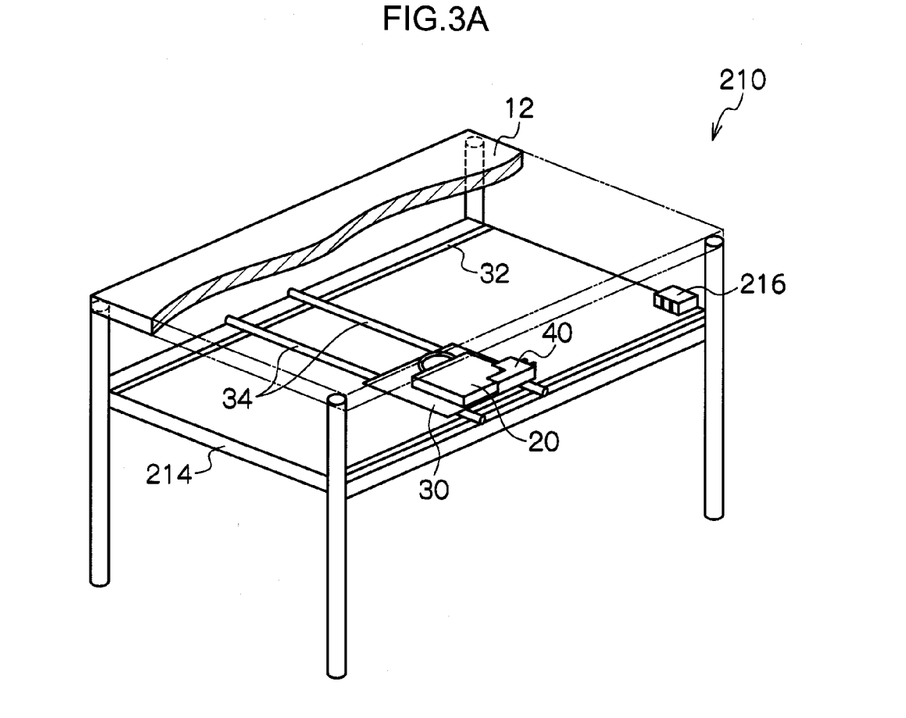
FIG. 3A is a schematic perspective view illustrating a radiographic imaging table according to a second exemplary embodiment.
Figure 3B:
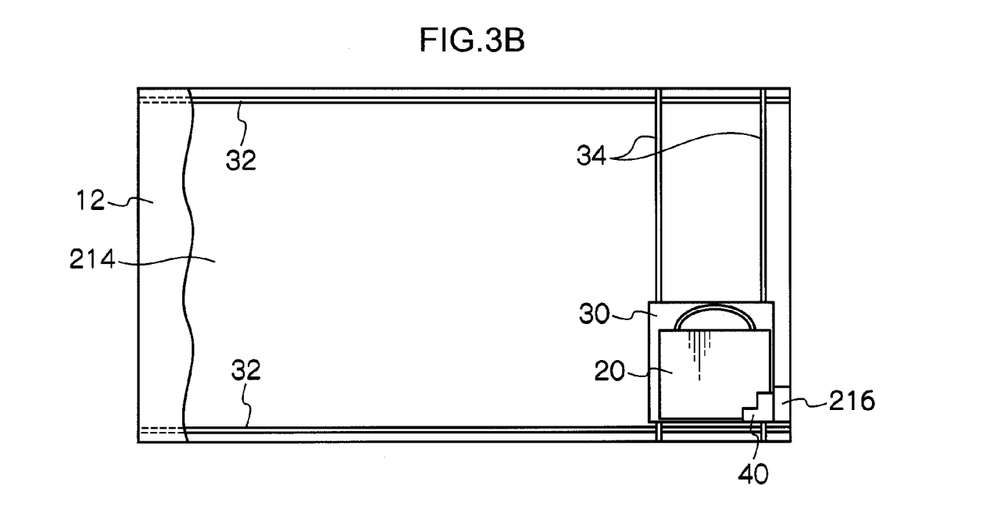
FIG. 3B is a plan view illustrating a cassette mounting plate of the radiographic imaging table according to the second exemplary embodiment.

As shown in FIG. 3A, a radiographic imaging table 210 according to the second exemplary embodiment has the same construction as that of the radiographic imaging table 10 according to the first exemplary embodiment in that a top board 12 and a cassette mounting plate 214 constitute a two-layer structure. However, as shown in FIGS. 3A and 3B, there is a difference in that a tray 30 for mounting the electronic cassette 20 thereon is disposed on the cassette mounting plate 214 and long-side-direction and short-side-direction rails 32 and 34 for moving the tray 30 on the cassette mounting plate 214 are disposed.

The long-side-direction rail 32 has a shape of a bar having a circular cross section and a length substantially the same as the long-side length of the cassette mounting plate 214. The long-side-direction rail 32 is fixed to a long-side-direction end region of the cassette mounting plate 214. The short-side-direction rail 34 is disposed through a first slider 36 (described later) on the long-side-direction rail 32.

The short-side-direction rail 34 has a shape of a bar having a circular cross section and a length substantially the same as the short-side length of the cassette mounting plate 214. The short-side-direction rail 34 is constructed with a pair of short-side-direction rails that are disposed in parallel to the short-side direction of the cassette mounting plate 214 and separated from each other by a distance corresponding to a width of the tray 30 described later.

Figure 4:
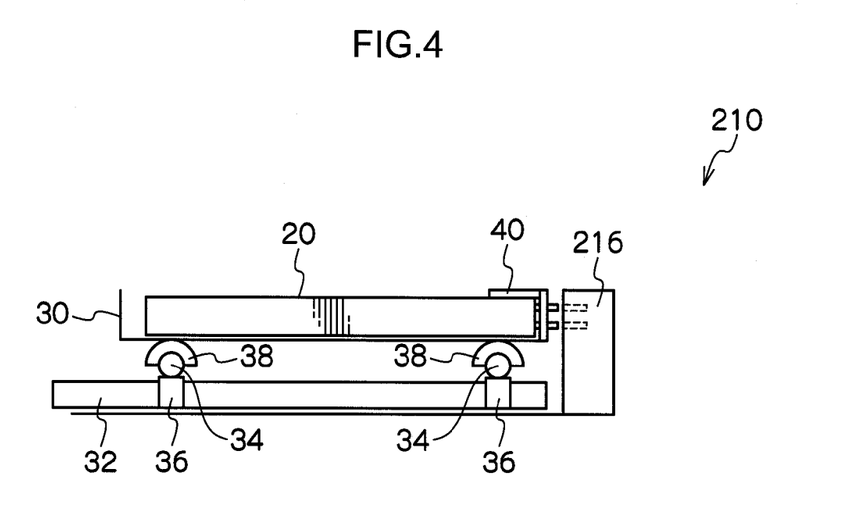
FIG. 4 is a side view illustrating a tray of the radiographic imaging table according to the second exemplary embodiment.

As shown in FIG. 4, the first sliders 36 are fixed to portions of the short-side-direction rails 34, where the short-side-direction rails 34 and the long-side-direction rails 32 are in contact with each other. The first slider 36 has a semi-cylindrical shape, and an inner diameter portion thereof has a shape coincident with a circumferential surface of the long-side-direction rail 32. The first slider 36 is superposed on the long-side-direction rail 32, so that the short-side-direction rail 34 fixed to the first slider 36 can be slid along the long-side-direction rail 32. In addition, stoppers (not shown) are provided to the ends of the long-side-direction rail 32 so as to limit the sliding of the short-side-direction rail 34.

The tray 30 on which the electronic cassette 20 can be mounted is disposed on the short-side-direction rails 34 through second sliders 38. The second sliders 38 are fixed to portions of the lower surface of the tray 30, where the short-side-direction rails 34 are in contact with the tray 30. The second slider 38 has a semi-cylindrical shape, and an inner diameter portion thereof has a shape coincident with a circumferential surface of the short-side-direction rail 34. The second slider 38 is superposed on the short-side-direction rail 34, so that the tray 30 fixed to the second slider 38 can be slid along the short-side-direction rail 34. In addition, stoppers (not shown) are provided to the ends of the short-side-direction rail 34 so as to limit the sliding of the tray 30.

Figure 5:
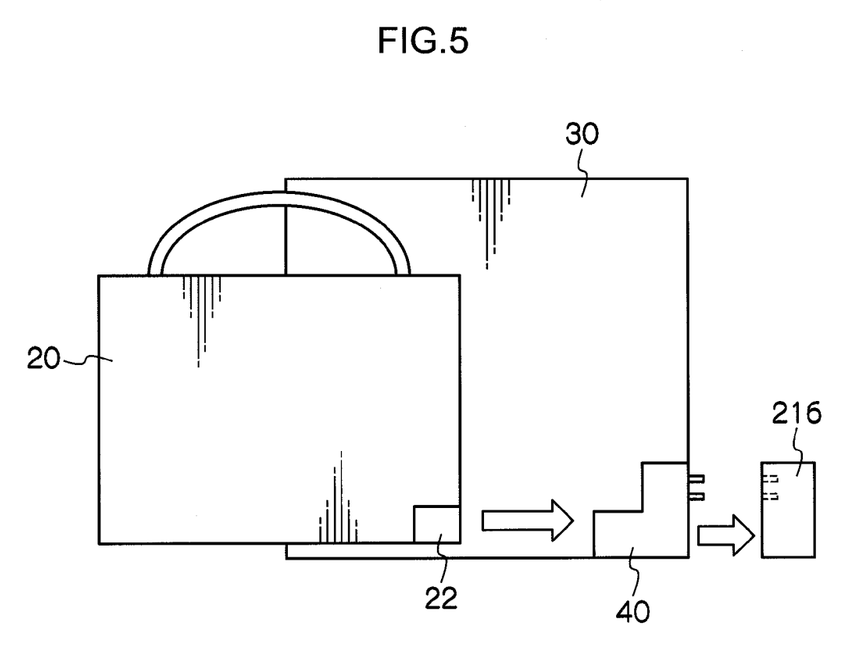
FIG. 5 is a schematic view illustrating a tray connection member of the radiographic imaging table according to the second exemplary embodiment.

In addition, as shown in FIG. 5, a tray connection member 40 is provided to a portion (for example, a corner) of the tray 30. The cassette connection member 22 is inserted into the tray connection member 40. An inner side of the tray connection member 40 can be connected to the cassette connection member 22 of the electronic cassette 20, and an outer side of the tray connection member 40 can be connected to a connector 216 provided to the cassette mounting plate 14. In addition, the connector 216 is connected through a cable to the AC power supply and the console. Accordingly, in the state that the cassette connection member 22 is connected to the tray connection member 40, the tray connection member 40 is connected to the connector 216, so that the electronic cassette 20 can be connected to the AC power supply and the console.

In addition, a lead plate as a radiation absorbing member is attached on an inner surface of the tray 30 on which the electronic cassette 20 is mounted, so that backward scattered radiation in the electronic cassette 20 can be absorbed. In this manner, since the lead plate is disposed on the inner surface of the tray 30, a lead plate provided to the electronic cassette 20 can be omitted. Therefore, the electronic cassette 20 can be constructed with a light weight. In addition, similarly to the radiographic imaging table according to the first exemplary embodiment, it is possible to reduce production costs in comparison with a case where a lead plate is disposed on the entire surface of the cassette mounting plate.

Next, operations of the radiographic imaging table 210 according to the second exemplary embodiment will be described.

At the time of imaging, the test object 19 is loaded on the top board 12. An operator mounts the electronic cassette 20 on the tray 30. While checking the loaded position of the test object 19 on the top board 12, the operator moves the tray 30 on which the electronic cassette 20 is mounted, to a corresponding position on the cassette mounting plate 214. At this time, the movement on the cassette mounting plate 214 in the short-side direction is performed by sliding the tray 30 along the short-side-direction rails 34. The movement on the cassette mounting plate 214 in the long-side direction is performed by sliding the short-side-direction rails 34 to which the tray 30 is fixed, along the long-side-direction rails 32.

Alternatively, before the test object 19 is loaded on the top board 12, the electronic cassette 20 may be mounted on the tray 30 in advance. In addition, the electronic cassette 20 may be mounted on the tray 30 so that the cassette connection member 22 is connected to the tray connection member 40.

When the imaging is ended, the operator moves the tray 30 on which the electronic cassette 20 is mounted, to the position where the connector 216 is disposed. In this step, if the cassette connection member 22 and the tray connection member 40 are not in the connected state, the cassette connection member 22 is first connected to the tray connection member 40, after which the tray connection member 40 is connected to the connector 216. Since the connector 216 is connected through a cable to the AC power supply, power is supplied from the AC power supply, so that the battery embedded in the electronic cassette 20 is charged through the tray connection member 40 with power as much as consumed power. In addition, since the connector 216 is connected through a cable to the console, in response to an operator's command of transmitting image data, the image data stored in a memory provided in the electronic cassette 20 is transmitted through the tray connection member 40 to the console.

When the charging of the battery or the transmitting of data is ended, the tray connection member 40 is disconnected from the connector 216. The electronic cassette 20 remains mounted on the tray 30 for the next imaging.

In addition, the console is connected to a radiology information system (RIS, not shown) which collectively manages radiographic image information or others handled in the department of radiology of a hospital. The RIS is connected to a hospital information system (HIS, not shown) which collectively manages medical information of a hospital. Therefore, in the console, since power that is to be consumed by the electronic cassette 20 in the next imaging can be requested, the charging with the power corresponding to the to-be-consumed power can be controlled.

In the radiographic imaging table according to the second exemplary embodiment, since the tray is moved along the long-side-direction rails and the short-side-direction rails, the electronic cassette mounted on the tray can be moved. In addition, since the tray connection member for connecting the cassette connection member with the connector is provided to the tray, in the state that the electronic cassette is mounted on the tray, the electronic cassette can be connected to the connector. In addition, the electronic cassette can be easily handled.

In addition, in the second exemplary embodiment, the long-side-direction rails and the short-side-direction rails are formed to have a shape of a bar having a circular cross-section, but the invention is not limited thereto. The rails may be formed to have a shape of a bar having a square or triangular cross-section. In this case, the first and second sliders are formed to have a shape coincident with the shape of the cross-section of the rail.

In addition, in the second exemplary embodiment, the construction where the long-side-direction rails are fixed to the cassette mounting plate has been described. However, alternatively, the short-side-direction rails are fixed to the short-side end region of the cassette mounting plate, and the longside-direction rails are disposed through the first sliders on the short-side-direction rails. In this case, the electronic cassette can be moved in the long-side direction by sliding the tray along the long-side-direction rails, and the electronic cassette can be moved in the short-side direction by moving the long-side-direction rails to which the tray is fixed, along the short-side-direction rails.

In addition, an image processing circuit board having a correction processing function or an image processing function for the radiographic image of the test object 19 imaged with the electronic cassette 20 is provided to the tray 30, so that there is no need for providing the functions to the inner portion of the electronic cassette. In this case, since only the function of capturing a radiographic image is provided to the electronic cassette 20, a small-sized, light-weight electronic cassette can be implemented.

Next, a modified example of the second exemplary embodiment will be described.

Figure 6A:
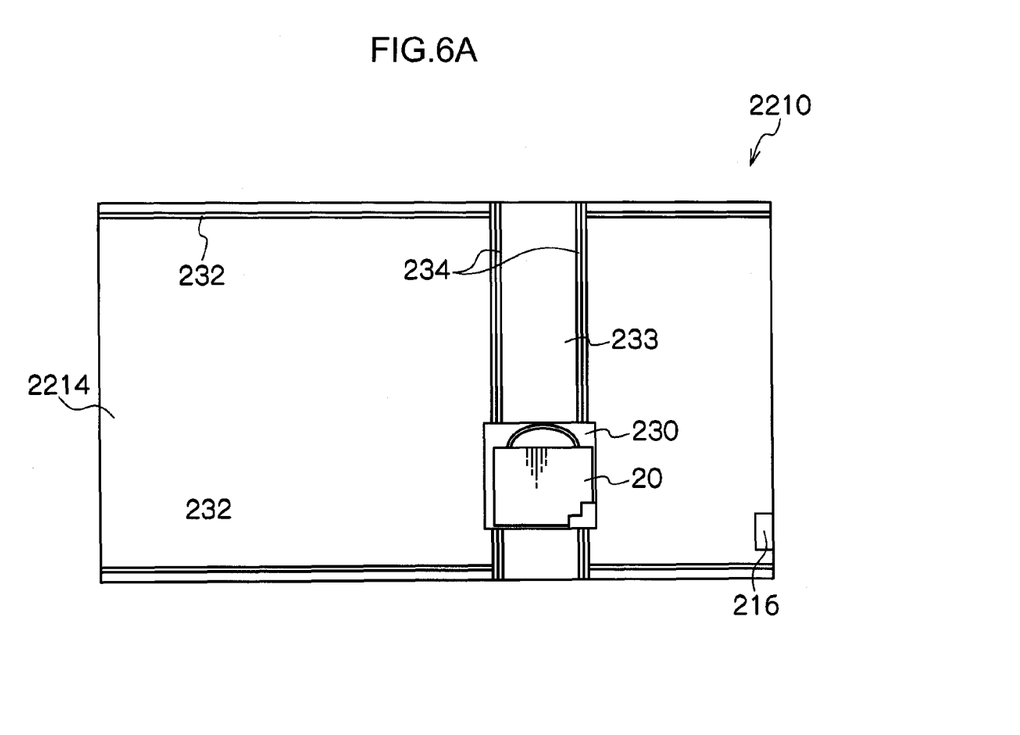
FIG. 6A is a plan view illustrating a cassette mounting plate of a radiographic imaging table according to a modified example of the second exemplary embodiment.
Figure 6B:
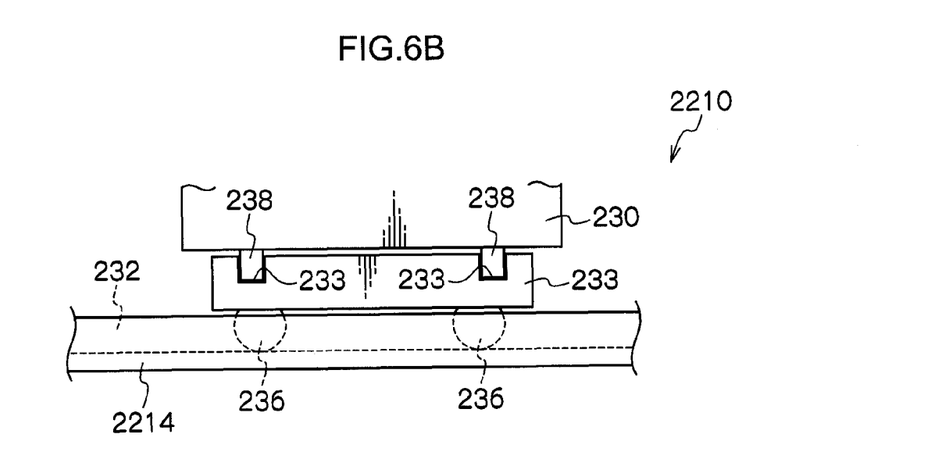
FIG. 6B is a side view illustrating a tray of the radiographic imaging table according to the modified example of the second exemplary embodiment.

As shown in FIG. 6, in a radiographic imaging table 2210 according to the modified example of the second exemplary embodiment, instead of rails, grooves are formed as tracks for moving a tray 230.

Long-side-direction grooves 232 having a length substantially the same as the long-side length of a cassette mounting plate 2214 are formed in long-side-direction end regions of the cassette mounting plate 2214.

In addition, a short-side-direction plate 233 having a length substantially the same as the short-side length of the cassette mounting plate 2214 and a width capable of mounting the tray 30 is disposed on the cassette mounting plate 2214. As shown in FIG. 6B, on a lower surface of the short-side-direction plate 233, first sliders 236 are disposed at positions corresponding to the long-side-direction grooves 232. Each of the first sliders 236 may be constructed with a cylindrical skid (roller). By sliding the skids in the long-side-direction grooves 232, the short-side-direction plate 233 can be slid along the long-side-direction grooves 232.

In addition, short-side-direction grooves 234 having a length substantially the same as the short-side length of the cassette mounting plate 2214 (that is, a length substantially the same as the long-side length of the short-side-direction plate 233) are formed in end regions of the short-side-direction plate 232 corresponding to the short-side direction of the cassette mounting plate 2214. In the tray 30, second sliders 238 are disposed at positions corresponding to the short-side-direction grooves 234. Each of the second sliders 238 may be constructed with a cylindrical skid. By sliding the skids in the short-side-direction grooves 234, the tray 230 can be slid along the short-side-direction grooves 234.

Accordingly, in the modified example, the electronic cassette can also be easily handled.

Next, a radiographic imaging table according to a third exemplary embodiment will be described. The same elements as those of the radiographic imaging table according to the second exemplary embodiment are denoted by the same reference numerals, and the description thereof is omitted.

Figure 7A:
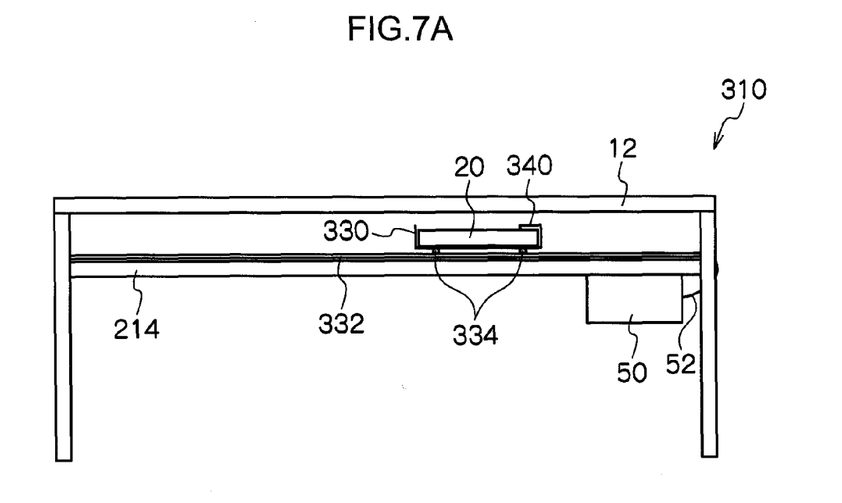
FIG. 7A is a schematic side view illustrating a radiographic imaging table according to a third exemplary embodiment.
Figure 7B:
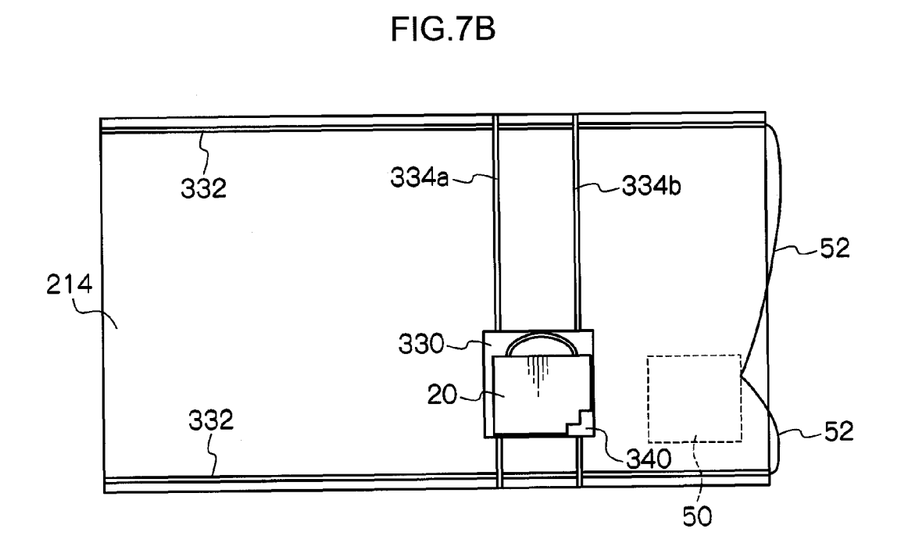
FIG. 7B is a plan view illustrating a cassette mounting plate of the radiographic imaging table according to the third exemplary embodiment.

As shown in FIG. 7, a radiographic imaging table 310 according to the third exemplary embodiment has the same construction as that of the radiographic imaging table 210 according to the second exemplary embodiment in that the top board 12 and the cassette mounting plate 214 constitute a two-layer structure and a tray 330, long-side-direction rails 332 and short-side-direction rails 334 are disposed on the cassette mounting plate 214. However, there is a difference in that the long-side-direction rails 332 and the short-side-direction rails 334 are also used as a power supply line and a data line.

First sliders (not shown) and second sliders (not shown) corresponding to the long-side-direction rails 332 and short-side-direction rails 334a and 334b and a tray connection member 340 are constructed with a conductive material. The second slider is fixed to a position which is in contact with the tray connection member 340 of the tray 330. In addition, on a lower surface of the cassette mounting plate 214, a power supply unit 50 connected to the AC power supply is disposed. The power supply unit 50 and the long-side-direction rails are connected to each other through wire lines.

When the tray connection member 340 and the cassette connection member 22 are connected to each other, power from the power supply unit 50 is supplied to the electronic cassette 20 through the long-side-direction rails 332, the first slider, the short-side-direction rail 334b, the second slider, and the tray connection member 340.

Next, operations of the radiographic imaging table 310 according to the third exemplary embodiment will be described.

At the time of imaging, the test object 19 is loaded on the top board 12. An operator mounts the electronic cassette 20 on the tray 330. At this time, the cassette connection member 22 and the tray connection member 340 are not connected to each other. While checking the loaded position of the test object 19 on the top board 12, the operator moves the tray 330 on which the electronic cassette 20 is mounted, to a corresponding position on the cassette mounting plate 214. At this time, the movement on the cassette mounting plate 214 in the short-side direction is performed by sliding the tray 330 along the shot-side-direction rails 334. The movement on the cassette mounting plate 214 in the long-side direction is performed by sliding the short-side-direction rails 334 to which the tray 330 is fixed, along the long-side-direction rails 332.

When the imaging is ended, the tray 330 remains in the position, or the tray 330 is moved to a position where the operator can easily handle it. In this state, the cassette connection member 22 is connected to the tray connection member 340. As a result, power corresponding to the consumed power is supplied from the power supply unit 50 through the long-side-direction rail 332, the first slider, the short-side-direction rail 334b, the second slider, and the tray connection member 340.

In addition, when the long-side-direction rail 332 is connected not to the power supply unit 50 but to the console, the cassette connection member 22 is connected to the tray connection member 340, so that the image data stored in the memory included in the electronic cassette 20 can be transmitted through the tray connection member 40 to the console.

When the charging of the battery or the transmitting of data is ended, the cassette connection member 22 is disconnected from the tray connection member 40. The electronic cassette 20 remains mounted on the tray 330 for the next imaging.

In addition, the console is connected to a radiology information system (RIS, not shown) which collectively manages radiographic image information or others handled in the department of radiology of a hospital. The RIS is connected to a hospital information system (HIS, not shown) which collectively manages medical information of a hospital. Therefore, in the console, since power that is to be consumed by the electronic cassette 20 in the next imaging can be requested, the charging with the power corresponding to the to-be-consumed power can be controlled.

In the radiographic imaging table according to the third exemplary embodiment, the charging of the electronic cassette and the transmitting of data can be performed without movement of the tray to the position of the connector disposed to a predetermined position, so that convenience can be improved.

In addition, in the third exemplary embodiment, the short-side-direction rail 334b is constructed with a conductive material. This construction is provided in order to simplify a connection mechanism between the tray connection member 340, the second slider, and the short-side-direction rails, by taking into consideration the construction where the tray connection member 340 is provided to the short-side-direction rail 334b. Alternatively, the short-side-direction rail 334a may be constructed with a conductive material, and a wire line between the tray connection member 340 and the second slider may be disposed on a rear surface of the tray 330.

In addition, since the charging of the electronic cassette and the communication with an external device can be performed through the rails, there is no need for providing the connector that is provided in the first and second exemplary embodiments. However, the connector may also be provided so that the charging and communication through the rails as well as the charging and communication through connection of the tray to the connector can be performed. Due to the construction, various types of electronic cassettes can be adaptively implemented.

Next, a radiographic imaging table according to a fourth exemplary embodiment will be described. The same elements as those of the radiographic imaging table according to the first to third exemplary embodiments are denoted by the same reference numerals, and the description thereof is omitted.

Figure 8:
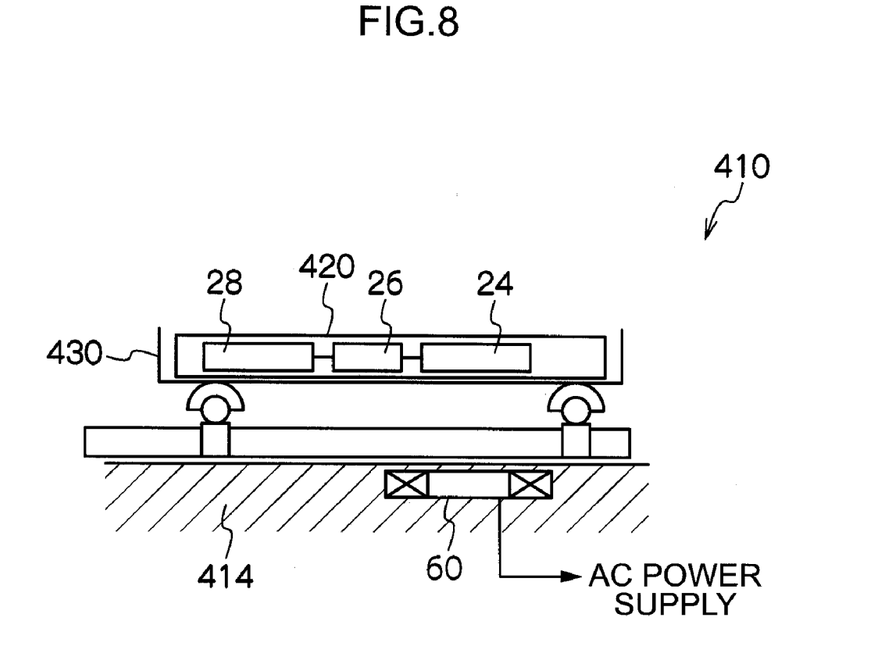
FIG. 8 is a side view illustrating a power transmitting coil of a radiographic imaging table according to a fourth exemplary embodiment.

As shown in FIG. 8, in a radiographic imaging table 410 according to the fourth exemplary embodiment, a power transmitting coil 60 functioning as a primary coil for charging a battery of an electronic cassette in a non-contact manner is disposed in an inner portion of a cassette mounting plate 414. The power transmitting coil 60 is connected to an AC power supply. In addition, the power transmitting coil 60 may be disposed on a lower surface of the cassette mounting plate 414 instead of an inner portion of the cassette mounting plate 414.

An electronic cassette 420 is provided with a power receiving coil 24 functioning as a secondary coil, a charging circuit 26 for rectifying an electromotive force generated in the power receiving coil 24, and a battery 28.

Next, operations of the radiographic imaging table 410 according to the fourth exemplary embodiment will be described.

At the time of imaging, the test object 19 is loaded on the top board 12. An operator mounts the electronic cassette 420 on a tray 430. While checking the loaded position of the test object 19 on the top board 12, the operator moves the tray 430 on which the electronic cassette 420 is mounted, to a corresponding position on the cassette mounting plate 414. At this time, the movement on the cassette mounting plate 414 in the short-side direction is performed by sliding the tray 430 along the short-side-direction rails 34. The movement on the cassette mounting plate 414 in the long-side direction is performed by sliding the short-side-direction rails 34 to which the tray 430 is fixed, along the long-side-direction rails 32.

When the imaging is ended, the tray 430 is moved to a charging position where the power transmitting coil 60 is disposed. Magnetic field is generated from the power transmitting coil 60 applied with the AC power due to electromagnetic induction. The electromotive force induced to the power receiving coil 24 by the magnetic field is rectified by the charging circuit 26, and the battery 28 is charged. When the charging of the battery 28 is ended, the tray 430 is moved from the charging position.

In this manner, in the radiographic imaging table according to the fourth exemplary embodiment, since the battery of the electronic cassette can be charged in a non-contact manner, there is no need for connecting the battery to the connector at the time of charging. Accordingly, convenience can be improved.

In addition, in the fourth exemplary embodiment, since the charging of the electronic cassette can be performed in a non-contact manner, there is no need for connection to the connector according to the first and second exemplary embodiments. However, a connector may be provided so as to perform communication with an external device or to perform the non-contact charging as well as the charging using a wire line connected to the connector. Due to the connector, various types of electronic cassettes can be adaptively implemented.

What is claimed is:

1. A radiographic imaging table comprising:
a test object mounting plate capable of allowing radiation to penetrate therethrough, on which a test object is mounted;
a detector mounting plate disposed under the test object mounting plate to movably mount a radiographic image detector which detects radiation penetrating the test object and the test object mounting plate, and which generates an image according to the detected radiation; and
a connection device disposed on the detector mounting plate such that it is connectable to the radiographic image detector in order to perform at least one of charging the radiographic image detector mounted on the detector mounting plate or facilitating communication between the radiographic image detector and an external device,
wherein the radiographic image detector is configured to be movable to an arbitrary position on the detector mounting plate and is operable to detect the radiation when the radiographic image detector is not connected to the connection device.

2. The radiographic imaging table of claim 1, further comprising a tray on which the radiographic image detector is mounted.

3. The radiographic imaging table of claim 2, wherein the tray is provided with a tray connection member which is used to connect the radiographic image detector with the connection device.

4. The radiographic imaging table of claim 2, wherein the detector mounting plate is provided with a pair of first tracks in one of a length or width direction thereof, a pair of second tracks are movably provided along the pair of first tracks, and the tray is provided so as to be capable of moving along the pair of second tracks in the other of the length or width direction of the detector mounting plate.

5. The radiographic imaging table of claim 4, wherein the first tracks and the second tracks comprise rails including a conductive member, and the charging of the radiographic image detector or the communication between the radiographic image detector and the external device is performed through the first tracks and the second tracks.

6. The radiographic imaging table of claim 2, wherein a radiation absorbing member is disposed on a surface of the tray.

7. The radiographic imaging table of claim 1, wherein a power supply unit, which supplies power in a non-contact manner to a power receiving member provided to the radiographic image detector through electromagnetic induction so that the power receiving member receives a power for charging an internal battery, is disposed at an inner portion of the detector mounting plate or under the detector mounting plate.

8. The radiographic imaging table of claim 1, wherein a radiation absorbing member is disposed on a surface of the detector mounting plate.

9. A radiographic imaging table comprising:
- a test object mounting plate capable of allowing radiation to penetrate therethrough, on which a test object is mounted;
- a detector mounting plate disposed under the test object mounting plate to movably mount a radiographic image detector which detects radiation penetrating the test object and the test object mounting plate, and which generates an image according to the detected radiation; and
- a pair of first rails in one of a length or width direction of the detector mounting plate, a pair of second rails movably provided along the pair of first rails, and a tray provided so as to be capable of moving along the pair of second rails in the other of the length or width direction of the detector mounting plate,
- wherein the first and second rails comprise a conductive member, and
- charging of the radiographic image detector or communication between the radiographic image detector and an external device is performed through the first and second rails.

10. The radiographic imaging table of claim 9, wherein a radiation absorbing member is disposed on a surface of the tray.

11. The radiographic imaging table of claim 9, wherein a power supply unit, which supplies power in a non-contact manner to a power receiving member provided to the radiographic image detector through electromagnetic induction so that the power receiving member receives a power for charging an internal battery, is disposed at an inner portion of the detector mounting plate or under the detector mounting plate.

12. The radiographic imaging table of claim 9, wherein a radiation absorbing member is disposed on a surface of the detector mounting plate.

13. A radiographic imaging table comprising:
- a test object mounting plate capable of allowing radiation to penetrate therethrough, on which a test object is mounted;
- a detector mounting plate disposed under the test object mounting plate to movably mount a radiographic image detector which detects radiation penetrating the test object and the test object mounting plate, and which generates an image according to the detected radiation; and
- a power supply unit disposed at an inner portion of the detector mounting plate or under the detector mounting plate, to supply power in a non-contact manner to a power receiving member provided to the radiographic image detector through electromagnetic induction so that the power receiving member receives a power for charging an internal battery.

14. The radiographic imaging table of claim 13, wherein a radiation absorbing member is disposed on a surface of the detector mounting plate.

* * * * *